United States Patent [19]

Himmele et al.

[11] 4,167,573

[45] Sep. 11, 1979

[54] METHOD OF CONTROLLING FUNGI WITH 3,5-DIMETHYL-PIPERIDIN-4-ONES

[75] Inventors: Walter Himmele, Walldorf; Karl-Heinz Koenig, Frankenthal; Norbert Goetz, Worms; Ernst-Heinrich Pommer, Limburgerhof, all of Fed. Rep. of Germany

[73] Assignee: BASF Aktiengesellschaft, Fed. Rep. of Germany

[21] Appl. No.: 901,418

[22] Filed: May 1, 1978

[30] Foreign Application Priority Data

May 7, 1977 [DE] Fed. Rep. of Germany ....... 2720612

[51] Int. Cl.$^2$ .............................................. A01N 9/22
[52] U.S. Cl. .................................... 424/267; 546/195; 546/203; 546/205; 546/216; 546/242
[58] Field of Search ...................... 260/293.89, 293.56; 424/267

[56] References Cited

U.S. PATENT DOCUMENTS

| | | | |
|---|---|---|---|
| 2,975,185 | 3/1961 | Anderson et al. | 260/293.56 |
| 3,366,638 | 1/1968 | Kühnis et al. | 260/293.89 |
| 3,468,885 | 9/1969 | Sanne et al. | 544/178 |
| 3,686,399 | 8/1972 | Sanne et al. | 424/248.4 |

OTHER PUBLICATIONS

Nazarov, I. et al., *J. Gen. Chem. USSR*, 25, 2209 (1955).

*Primary Examiner*—Alan L. Rotman
*Assistant Examiner*—Richard A. Schwartz
*Attorney, Agent, or Firm*—Keil & Witherspoon

[57] ABSTRACT

Valuable novel 3,5-dimethyl-piperidin-4-one compounds, substituted at the nitrogen by a long-chain radical, which have a good fungicidal action, and a process for combating fungi by means of these compounds.

1 Claim, No Drawings

METHOD OF CONTROLLING FUNGI WITH 3,5-DIMETHYL-PIPERIDIN-4-ONES

The present invention relates to novel piperidin-4-one derivatives and their salts, to fungicides which contain these compounds, and to processes for combating phytopathogenic fungi by means of these compounds.

German Pat. Nos. 1,164,152 and 1,173,722 disclose that N-alkyl-substituted and N-cycloalkyl-substituted morpholines have a fungicidal action.

We have found that piperidin-4-ones of the general formula

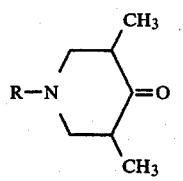

where R is a straight-chain or branched alkyl of 8 to 20 carbon atoms or is cycloalkyl, cycloalkylalkyl, alkylcycloalkylalkyl, bicycloalkyl, alkylbicycloalkyl, tricycloalkyl or tetracycloalkyl of 8 to 20 carbon atoms and their salts have a good fungicidal action.

Examples of radicals R of 8 to 20 carbon atoms are 2-ethyl-hex-1-yl, n-decyl, 5-ethyl-non-2-yl, 6-ethyl-dec-3-yl, 2-butyl-oct-1-yl, tridec-2-yl, tridec-3-yl, tridec-5-yl, tridec-7-yl, 2-methyl-dodec-1-yl, pentadec-1-yl, hexadec-1-yl, octadec-1-yl, 2-ethyl-5-cyclohexyl-pent-1-yl, cyclododecyl-methyl, cyclooctyl, 3,5-dimethyl-cyclohex-1-yl, 3-[(4-isopropyl)-cyclohex-1-yl]-2-methyl-prop-1-yl, 4-[(2,2,4-trimethyl)-cyclohex-1-yl]-but-2-yl, 3-[(4-tert.-butyl)-cyclohex-1-yl]-2-methyl-prop-1-yl, 3-[(4-tert.-butyl)-cyclohex-1-yl]-3-methyl-prop-1-yl, 5-[(4-tert.-butyl)-cyclohex-1-yl]-2,4-dimethyl-pent-1-yl and the like.

The novel 3,5-dimethylpiperidin-4-ones, as such or as their salts with inorganic acids, eg. hydrohalic acids (hydrochloric acid or hydrobromic acid), sulfuric acid, nitric acid and phosphoric acid, or with organic acids, e.g., formic acid, acetic acid, butyric acid, acrylic acid, oxalic acid, adipic acid, lactic acid, tartaric acid, citric acid, trichloroacetic acid, stearic acid, oleic acid, diisopropyldithiophosphoric acid, p-toluenesulfonic acid, dodecylbenzenesulfonic acid and dodecanesulfonic acid, can be used as fungicides.

The N-substituted 3,5-dimethylpiperidin-4-ones are prepared by, for example, reacting the corresponding primary amines with 2,4-dimethylpenta-1,4-dien-3-one

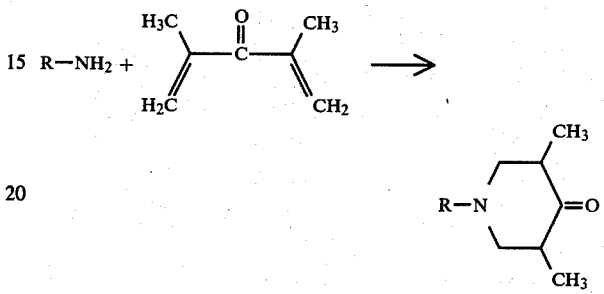

where R has the above meanings.

The primary amines (R—NH$_2$) required as starting materials may be prepared from the corresponding aldehydes or ketones by reductive amination (Houben-Weyl "Methoden der organischen Chemie" volume 11/1, page 602 et seq.).

2,4-Dimethylpenta-1,4-dien-3-one may be synthesized from diisopropyl ketone by bromination, and elimination of hydrogen bromide (O. Sorokin, Izv. Akad. Nauk USSR 1961, 460–466), or by the method described in Houben-Weyl "Methoden der organischen Chemie" volume 7/2a, page 743 or by S. F. Reed, J. Org. Chem. 27 (1962), 4,116.

The Table which follows lists some examples of the compounds according to the invention.

| No. | Compound (X = piperidinone) | b.p. (°C.)/mm Hg | m.p. (°C.) |
|---|---|---|---|
| 1 | H$_3$C~~~~~~X | 135/5.0 | |
| 2 | H$_3$C~~~~~~X . HCl | | 125 |
| 3 | (H$_3$C)$_3$C-CH(CH$_3$)-CH$_2$-X | 120/5.0 | |
| 4 | (H$_3$C)$_3$C-CH(CH$_3$)-CH$_2$-X . HCl | | 179 |
| 5 | (H$_3$C)$_3$C-CH(CH$_3$)-CH$_2$-X . HBr | | 166 |
| 6 | (H$_3$C)$_2$CH-CH$_2$-CH(CH(CH$_3$)$_2$)-X | 143/5.0 | |

| No. | Compound (X = ![piperidone])  | b.p. (°C.)/mm Hg | m.p. (°C.) |
|---|---|---|---|
| 7 | H₃C-CH(CH₂CH₃)-CH₂-CH(-)-CH₂-X (2-ethylhexyl type) | 135/5 | |
| 8 | H₃C-(CH₂)₁₁-X | 162/0.3 | |
| 9 | H₃C-(CH₂)₁₃-X · HCl | | 94 |
| 10 | H₃C-(CH₂)₁₃-X · CH₃COOH | oily | |
| 11 | H₃C-(CH₂)₁₅-X | 155/0.01 | |
| 12 | i-C₁₃H₂₇—X (isomer mixture) | 128/0.01 | |
| 13 | i-C₁₃H₂₇—X · C₁₂H₂₅—C₆H₄—SO₃H (isomer mixture) | oily | |
| 14 | H₃C-(CH₂)ₙ-X | 160/0.01 | |
| 15 | H₃C-CH(X)-(CH₂)ₙ-CH₃ | 136/0.1 | |
| 16 | H₃C-(CH₂)ₙ-X | 173/0.1 | |
| 17 | (CH₃)₂CH-CH₂-CH(CH₃)-CH₂-CH(CH₃)-X | 128/0.05 | |
| 18 | (CH₃)₂CH-CH₂-CH(CH₃)-CH₂-CH(CH₃)-X · C₁₂H₂₅—C₆H₄—SO₃H | oily | |
| 19 | (CH₃)₂CH-CH(CH₃)-(CH₂)₂-C(CH₃)(CH₂CH₃)-X | 104/0.4 | |
| 20 | (CH₃)₂CH-CH(CH₃)-CH₂-CH(CH₃)-CH₂-CH(CH₃)-CH₂-CH(CH₃)-X | 171/0.01 | |
| 21 | (CH₃)₂CH-CH(CH₃)-CH₂-CH(CH₃)-CH₂-CH(CH₃)-CH₂-CH(CH₃)-X · C₁₂H₂₅—C₆H₄—SO₃H | pasty | |
| 22 | (CH₃)₂CH-CH(CH₃)-CH₂-CH(CH₃)-CH₂-C(CH₃)(CH₂CH₃)-X | 150/0.01 | |
| 23 | 2,6-dimethylcyclohexyl-X | 113/0.5 | |
| 24 | cyclic (adamantyl-type)-X | 173/0.3 | |

-continued

Compound (X = —N⟨piperidinone with 3,5-dimethyl and 4-oxo⟩)

| No. | | b.p. (°C.)/mm Hg | m.p. (°C.) |
|---|---|---|---|
| 25 | [cyclo structure]—X · HCl | | 153 |
| 26 | [cyclo structure]—X · CH₃ · COOH | oily | |
| 27 | [cyclohexyl-CH(CH₃)CH₂]—X · HCl | | 176 |
| 28 | [(CH₃)₃C-cyclohexyl-CH₂CH(CH₃)]—X | 180–184/5 | |
| 29 | [(CH₃)₃C-cyclohexyl-CH₂CH(CH₃)]—X · HCl | | 170 |
| 30 | [trimethylcyclohexyl-CH₂CH(CH₃)]—X | 154/0.01 | |
| 31 | [trimethylcyclohexyl-CH₂CH(CH₃)]—X · C₁₂H₂₅—C₆H₄—SO₃H | pasty | |
| 32 | [bicyclic terpene]—X' | 146/0.5 | |
| 33 | [bicyclic terpene]—X · HCl | | 205 |
| 34 | [bicyclic terpene]—X | 190/5 | |
| 35 | [bicyclic terpene]—X · HCl | | 190 |

-continued

| No. | Compound (X = piperidinone with 3,5-dimethyl) | b.p. (°C.)/mm Hg | m.p. (°C.) |
|---|---|---|---|
| 36 | bicyclopentyl–X | 158/5 | |
| 37 | bicyclopentyl–X . HCl | | 252 |
| 38 | bicyclopentyl–X . C₁₂H₂₅–C₆H₄–SO₃H | | 125 |
| 39 | norbornyl–X | 145/5 | |
| 40 | norbornyl–X . HCl | | 242 |
| 41 | decahydronaphthyl–X | 136–140/0.3 | |
| 42 | decahydronaphthyl–X . HCl | | 221 |
| 43 | decahydronaphthyl–X | 170/0.3 | |

EXAMPLE 1

53.9 parts by weight of 6,10,14-trimethyl-2-aminopentadecane are dissolved in 200 parts of methanol. A solution of 22 parts of 2,4-dimethyl-penta-1,4-dien-3-one in 100 parts of methanol is added at room temperature and this mixture is then heated at the reflux temperature (65° C.) for 3 hours. The reaction product is worked up by distillation, giving 67.5 parts ( 89% of theory) of N-(6,10,14-trimethyl-pentadec-2-yl)-3,5-dimethyl-piperidin-4-one, boiling point=171° C./0.01 mm Hg (active ingredient No. 20).

The novel active ingredients can be converted to the conventional formulations, e.g., solutions, emulsions, suspensions, powders, pastes and granules. These may be prepared in the conventional manner, e.g., by mixing the active ingredient with a solvent and/or carrier, with or without addition of an emulsifier or dispersant, and, where water is used as the diluent, with or without addition of an organic auxiliary solvent. Examples of the above ingredients are, essentially: solvents—aromatics (e.g., xylene and benzene), chloroaromatics (e.g., chlorobenzenes), paraffins (e.g., petroleum fractions), alcohols (e.g., methanol and butanol), amines (e.g., ethanolamine and dimethylformamide) and water; carriers—natural rock powders (e.g., kaolins, aluminas, talc and chalk) and synthetic rock powders (e.g., highly disperse silica and silicates); emulsifiers—non-ionic and anionic emulsifiers (e.g., polyoxyethylene fatty alcohol ethers, alkylsulfonates and arylsulfonates); dispersants—lignin, sulfite waste liquors and methylcellulose.

The formulations in general contain from 0.1 to 95 percent by weight of active ingredient, preferably from 0.5 to 90%. The formulations, or the ready-to-use compositions prepared therefrom, e.g., solutions, emulsions, suspensions, powders, pastes or granules, may be employed by conventional methods, e.g., by spraying, atomizing, dusting, scattering, dressing or watering.

The fungicides of the invention can also be used conjointly with other active ingredients, e.g., herbicides, insecticides, growth regulators, bactericides, fungicides and fertilizers.

The novel active ingredients may be used for combating fungi in agriculture, especially powdery mildew fungi, e.g., *Erysiphe graminis* on cereals, *Uncinula necator* on vines, *Podosphaera leucotricha* on apples, *Sphaerotheca fuliginea* on roses and *Erysiphe cichoriacearum* on cucumbers. They are also effective against cereal rust caused by species of Puccinia.

The amounts required for combating phytopathogenic fungi are generally from 0.05 to 2 kg of active ingredient per hectare of cultivated area.

EXAMPLE 2

Powdery mildew of barley

Leaves of barley seedlings grown in pots are sprayed with an aqueous emulsion containing a mixture of 80% by weight of active ingredient and 20% by weight of emulsifier and after the spray coating has dried the leaves are dusted with oidia (spores) of powdery mildew of barley (*Erysiphe graminis* var. hordei). The test plants are then placed in a greenhouse at from 20° to 22° C. and from 75 to 80% relative atmospheric humidity. The degree of development of the mildew fungi is assessed after 10 days.

| Active ingredient No. | Infection of the leaves after spraying with an X% strength liquor of active ingredient | |
|---|---|---|
| | X = 0.1 | X = 0.05 |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 14 | 0 | 0 |
| 15 | 0 | 0 |
| 16 | 0 | 0 |
| 17 | 0 | 0 |
| 18 | 0 | 0 |
| 20 | 0 | 0 |
| 21 | 0 | 0 |
| 25 | 0 | 0 |
| 26 | 0 | 0 |
| 28 | 0 | 0 |
| 29 | 0 | 0 |
| 31 | 0 | 0 |
| 34 | 0 | 0 |
| 35 | 0 | 0 |
| 36 | 0 | 0 |
| 37 | 0 | 0 |
| 39 | 0 | 0 |
| 40 | 0 | 0 |
| 41 | 0 | 0 |
| 42 | 0 | 0 |
| 43 | 0 | 0 |
| Control (untreated) | 4 | |

0 = no fungal infection, graded up to 5 = total infection.

EXAMPLE 3

Powdery mildew of wheat

Leaves of wheat seedlings, of the Jubilar variety, grown in pots are sprayed with an aqueous emulsion containing a mixture of 80% by weight of active ingredient and 20% by weight of emulsifier and after the spray coating has dried the leaves are dusted with oidia (spores) of powdery mildew of wheat (*Erysiphe graminis* var. tritici). The test plants are then placed in a greenhouse at from 20° to 22° C. and from 75 to 80% relative atmospheric humidity. The degree of development of the mildew is assessed after 10 days.

| Active ingredient No. | Infection of the leaves after spraying with an X% strength liquor of active ingredient | |
|---|---|---|
| | X = 0.1 | X = 0.05 |
| 1 | 0 | 0 |
| 2 | 0 | 0 |
| 3 | 0 | 3 |
| 4 | 0 | 3 |
| 6 | 0 | 0 |
| 7 | 0 | 0 |
| 14 | 0 | 2 |
| 15 | 0 | 2 |
| 27 | 0 | 0 |
| 28 | 0 | 0 |
| 29 | 0 | 0 |
| 31 | 1 | 2 |
| 32 | 0 | 0 |
| 33 | 0 | 0 |
| 34 | 0 | 0 |
| 35 | 0 | 2 |
| 36 | 0 | 2 |
| 37 | 0 | 0 |
| 39 | 0 | 0 |
| 40 | 2 | 2 |
| Control (untreated) | 4 | |

0 = no fungal infection, graded up to 5 = total infection.

EXAMPLE 4

Powdery mildew of cucumber

Leaves of cucumber seedlings grown in pots are sprayed with an aqueous emulsion containing a mixture of 80% of active ingredient and 20% of emulsifier and after the spray coating has dried the leaves are dusted with oidia (spores) of powdery mildew of cucumber (*Erysiphe cichoriacearum*). The test plants are then placed in a greenhouse at from 20° to 22° C. and from 75 to 80% relative atmospheric humidity. The degree of development of the mildew fungi is assessed after 10 days.

| After ingredient No. | Infection of the leaves after spraying with a 0.1% strength liquor of active ingredient |
|---|---|
| 1 | 0 |
| 2 | 0 |
| 5 | 2 |
| 6 | 2 |
| 8 | 2 |
| 15 | 0 |
| 16 | 2 |
| 18 | 0 |
| 23 | 0 |
| 26 | 0 |
| 28 | 0 |
| 29 | 0 |
| 34 | 0 |
| 36 | 0 |
| 37 | 2 |

-continued

| After ingredient No. | Infection of the leaves after spraying with a 0.1% strength liquor of active ingredient |
|---|---|
| 39 | 2 |
| 40 | 0 |
| 41 | 0 |
| 42 | 0 |
| 43 | 2 |
| Control (untreated) | 5 |

0 = no fungal infection, graded up to 5 = total infection.

EXAMPLE 5

Crown rust of oats

Leaves of pot-grown oat plants artificially infected with spores of crown rust of oats (*Puccinia coronata*) and placed for 48 hours at from 20° to 25° C. in a chamber in which the atmosphere is saturated with water vapor. The plants are then sprayed with aqueous spray liquors which contain a mixture of 80% by weight of the active ingredient to be tested and 20% by weight of sodium lignin-sulfonate, dissolved or emulsified in the water, and are placed in a greenhouse at from 20° to 22° C. and from 75 to 80% relative atmospheric humidity. After 10 days, the degree of development of the rust fungi is assessed.

| Active ingredient No. | Infection of the leaves after spraying with a liquor containing 0.1% of active ingredient |
|---|---|
| 28 | 0 |
| 29 | 0 |
| 35 | 0 |
| 37 | 0 |
| N-Tridecyl-2,6-dimethyl-morpholine (known) | 2 |
| N-Cyclododecyl-2,6-dimethyl-morpholine (known) | 3 |
| Control (untreated) | 4 |

0 = no fungal infection, graded up to 5 = total infection.

EXAMPLE 6

90 parts by weight of compound 1 are mixed with 10 parts by weight of N-methyl-α-pyrrolidone and a solution suitable for use in the form of very fine droplets is obtained.

EXAMPLE 7

20 parts by weight of compound 3 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of calcium dodecylbenzenesulfonate and 5 parts by weight of the adduct of 40 moles of ethylene oxide with 1 mole of castor oil. On pouring this solution into 100,000 parts by weight of water, and finely dispersing it therein, an aqueous dispersion containing 0.02% by weight of active ingredient is obtained.

EXAMPLE 8

20 parts by weight of compound 6 are dissolved in a mixture consisting of 40 parts by weight of cyclohexanone, 30 parts by weight of isobutanol, 20 parts by weight of the adduct of 7 moles of ethylene oxide with 1 mole of isooctyphenol and 10 parts by weight of the adduct of 40 moles of ethylene oxide with 1 mole of castor oil. On pouring this solution into 100,000 parts by weight of water, and finely dispersing it therein, an aqueous dispersion containing 0.02% by weight of active ingredient is obtained.

EXAMPLE 9

20 parts by weight of compound 7 are dissolved in a mixture which consists of 25 parts by weight of cyclohexanol, 65 parts by weight of a mineral oil fraction of boiling point 210°–280° C. and 10 parts by weight of the adduct of 40 moles of ethylene oxide with 1 mole of castor oil. On pouring this solution into 100,000 parts by weight of water, and finely dispersing it therein, an aqueous dispersion containing 0.02% by weight of active ingredient is obtained.

EXAMPLE 10

20 parts by weight of active ingredient 8 are thoroughly mixed with 3 parts by weight of sodium diisobutylnaphthalene-α-sulfonate, 17 parts by weight of the sodium salt of a ligninsulfonic acid obtained from a sulfite waste liquor and 60 parts by weight of silica gel powder, and the mixture is milled in a hammer mill. On finely dispersing the mixture in 20,000 parts by weight of water, a spray liquor containing 0.1 percent by weight of active ingredient is obtained.

EXAMPLE 11

3 parts by weight of compound 2 are intimately mixed with 97 parts by weight of finely divided kaolin. A dusting agent containing 3% by weight of active ingredient is thus obtained.

EXAMPLE 12

30 parts by weight of compound 4 are intimately mixed with a mixture of 92 parts by weight of silica gel powder and 8 parts by weight of paraffin oil which has been sprayed onto the surface of the silica gel. A formulation of the active ingredient which clings well is obtained.

EXAMPLE 13

40 parts by weight of active ingredient 11 are intimately mixed with 10 parts by weight of the sodium salt of a phenolsulfonic acid/urea/formaldehyde condensate, 2 parts by weight of silica gel and 48 parts by weight of water. A stable aqueous dispersion is obtained. On dilution with 100,000 parts by weight of water, an aqueous dispersion containing 0.04 percent by weight of active ingredient is obtained.

EXAMPLE 14

20 parts of active ingredient 12 are intimately mixed with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

We claim:

1. A process for combating fungi, wherein the area to be protected against fungal attack is treated with a fungicidally effective amount of a 3,5-dimethyl-piperidin-4-one derivative of the general formula

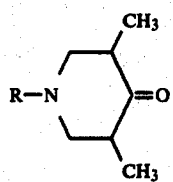
where R is straight-chain or branched alkyl of 8 to 20 carbon atoms or is cycloalkyl, cycloalkylalkyl, alkylcycloalkylalkyl, bicycloalkyl, alkylbicycloalkyl, tricycloalkyl or tetracycloalkyl of 8 to 20 carbon atoms or with a salt of this compound.
* * * * *